United States Patent [19]

MacGregor

[11] Patent Number: 5,342,702
[45] Date of Patent: Aug. 30, 1994

[54] SYNERGISTIC PROCESS FOR THE PRODUCTION OF CARBON DIOXIDE USING A COGENERATION REACTOR

[75] Inventor: Norman J. MacGregor, Kincardine, Canada

[73] Assignee: Integrated Energy Development Corp., Kincardine, Canada

[21] Appl. No.: 945

[22] Filed: Jan. 5, 1993

[51] Int. Cl.$^5$ .......................... H01M 8/00; H01M 8/18
[52] U.S. Cl. ......................................... 429/13; 429/21; 204/DIG. 4; 204/129; 423/245.1; 423/248; 60/39.182; 568/671
[58] Field of Search .......................... 204/129, DIG. 4; 60/39.182; 423/245.1, 248; 568/671, 840; 429/17, 21

[56] References Cited

U.S. PATENT DOCUMENTS

| | | | |
|---|---|---|---|
| 2,482,284 | 9/1949 | Michael et al. | 260/449 |
| 3,095,699 | 7/1963 | Baver | 60/39.02 |
| 4,528,811 | 7/1985 | Stahl | 60/39.07 |
| 4,534,772 | 8/1984 | Reichl | 44/53 |
| 4,592,762 | 6/1986 | Babu et al. | 48/197 R |
| 4,699,632 | 10/1987 | Babu et al. | 48/197 R |
| 4,773,981 | 8/1988 | Bidwell | 204/129 |
| 4,810,417 | 3/1989 | Diemer et al. | 252/373 |
| 4,833,170 | 5/1989 | Agee | 518/703 |
| 4,899,544 | 2/1990 | Boyd | 60/618 |
| 4,942,734 | 7/1990 | Markbreiter et al. | 60/39.02 |
| 5,023,276 | 6/1991 | Yarrington et al. | 514/703 |
| 5,025,631 | 6/1991 | Garbo | 60/655 |
| 5,026,529 | 6/1991 | Harandi et al. | 422/190 |
| 5,070,016 | 12/1991 | Hallberg | 435/132 |
| 5,132,007 | 7/1992 | Meyer et al. | 208/427 |

*Primary Examiner*—Kathryn Gorgos
*Attorney, Agent, or Firm*—Bereskin & Parr

[57] ABSTRACT

A synergistic process for the production of carbon dioxide comprises preparing a feed stream comprising an organic combustible fuel and hydrogen; introducing the feed stream and air into a cogeneration reactor for combusting the feed stream and producing steam, electricity and stack gases containing carbon dioxide; using at least a portion of said electricity to electrolyze water to produce hydrogen and oxygen; recovering the hydrogen and oxygen and recycling at least a portion of the hydrogen for preparation of the feed stream; and, recovering the carbon dioxide from the stack gases.

21 Claims, 4 Drawing Sheets

SYNERGISTIC PROCESS FOR THE PRODUCTION OF CARBON DIOXIDE USING A COGENERATION REACTOR

FIELD OF THE INVENTION

This invention relates to an integrated process for producing carbon dioxide via a cogeneration process. In particular, this invention pertains to a cogeneration process using a hydrogen enhanced fuel source.

BACKGROUND OF THE INVENTION

Various processes are known for the production of carbon dioxide. In addition, carbon dioxide also occurs as a natural by-product of the combustion of organic materials. One disadvantage of many current processes is that the carbon dioxide may be very dilute, and accordingly, it is not economically viable to recover the carbon dioxide. A second disadvantage with current processes is that the combustion gases may contain substantial amounts of other gases and particulates which complicate the recovery of the carbon dioxide, and accordingly, mitigate against the recovery of the carbon dioxide.

In terms of the volume of discharge, carbon dioxide is one of the main green house gases which is released into the atmosphere by industry today. However, on a mole by mole basis, unburned gases, such as methane are one magnitude more effective as green house gases than carbon dioxide. Accordingly, one problem with the combustion of organic compounds is the production of green house gases. A second problem with the combustion of organic compounds is that incomplete combustion may occur releasing higher potency green house gases into the atmosphere.

SUMMARY OF THE INVENTION

It has been found that these problems can be reduced by preparing a feed stream comprising an organic combustible fuel and hydrogen, introducing the feed stream, air and optionally oxygen into a cogeneration reactor for combusting the feed stream and producing steam, electricity and stack gases containing carbon dioxide; using at least a portion of said electricity to electrolyze water to produce hydrogen and oxygen; recovering the hydrogen and recycling at least a portion thereof for preparation of said feed stream; recovering the oxygen and optionally recycling at least a portion thereof for introduction into the reactor; and recovering the carbon dioxide from the stack gases.

In one embodiment, the organic combustible fuel is a gaseous fuel and may be natural gas or methane. The electrolysis of the water occurs in off-peak hours. The oxygen is stored for introduction into the reactor at a controlled rate. The hydrogen is temporarily stored for introduction, at least in part, into a stream of natural gas to produce hythane which may be stored for later use or used immediately.

The amount of hydrogen which is added to the organic combustible fuel may vary from about 10% to about 20%, preferably about 15% on a volume basis. The amount of oxygen which is added to the combustion air fed to the reactor may vary from about 0% to about 30% and, more preferably about 15% on a volume basis. In one embodiment, at least a portion of the stack gases are recycled to the cogeneration reactor and a higher concentration of oxygen is fed to the reactor. In particular, the combustion air may contain over 30% oxygen on a volume basis.

The stack gases produced from the combustion of the fuel have a relatively high percentage of carbon dioxide. The carbon dioxide may then be recovered and used in the production of methanol. A portion of the hydrogen from the electrolysis process may be combined with the carbon dioxide to produce methanol. At least a portion of the methanol may then be reformed to produce methyl tertiary butyl ether (MTBE).

In a further embodiment, municipal solid wastes by themselves or together with wood waste and agricultural fibrous waste, such as straw and low-quality hay, are used to provide a source of cellulose. A portion of the hydrogen is used to produce ammonia, which is then used to prepare cellulose for conventional fermentation. Alternately, some process steam from the cogeneration reactor may be used to prepare cellulose for conventional fermentation. Some process steam from the cogeneration process may be used to prepare ethanol from the cellulose. The ethanol may then be reformed to produce ethyl tertiary butyl ether (ETBE). The carbon dioxide produced in the fermentation process may be combined with hydrogen to produce an additional supply of methanol.

The process of the instant invention provides an integrated process for producing carbon dioxide for industrial use via a cogeneration process. The enhanced feed stream and, optional, enhanced air stream, which are obtained via electrolysis using off-peak electricity, produces cleaner stack emissions thus reducing the release of uncombusted organic fuel and permitting the recovery of carbon dioxide for industrial use.

BRIEF DESCRIPTION OF THE DRAWINGS

This and other advantages of the instant invention may be more completely and fully understood by means of the following description of the accompanying drawings of the preferred embodiment of the process which is the subject of this invention in which.

DESCRIPTION OF THE PREFERRED EMBODIMENT

Figure 2:
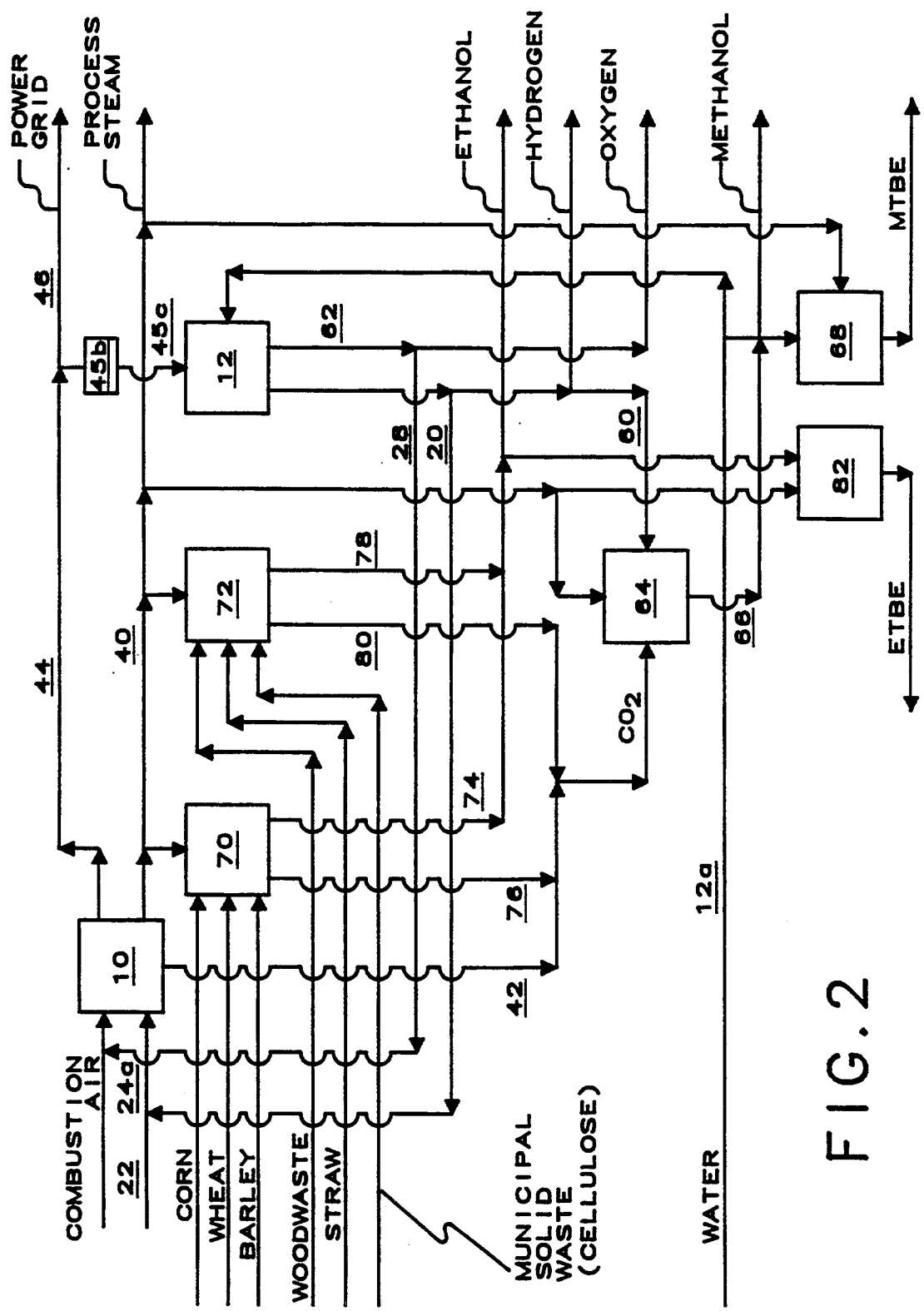
FIG. 2 is a schematic of a second embodiment of this process showing subsequent production of methanol and ethanol.

By reference to FIG. 2, the process utilizes a cogeneration reactor 10 and electrolysis cell 12.

Figure 1:
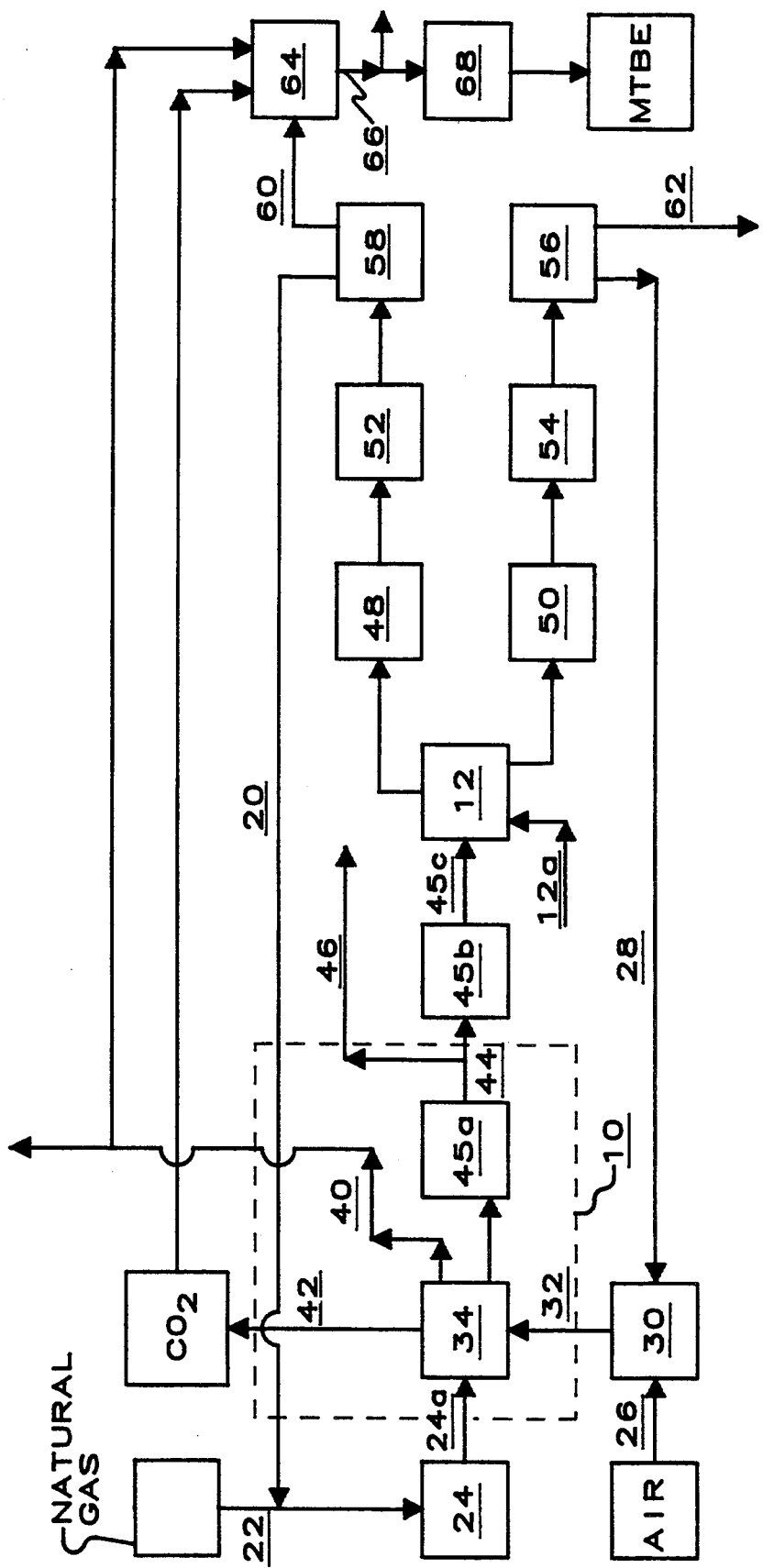
FIG. 1 is a schematic of a process flow sheet of one embodiment of this invention.

As shown in more detail in FIG. 1, cogeneration reactor 10 may be any cogeneration reactor known in the art. In particular, the cogeneration reactor may be either a single cycle or a combined cycle reactor. More preferably, a combined cycle reactor is utilized.

The fuel which is fed to the cogeneration reactor may be an organic combustible fuel. Preferably, the organic combustible fuel is a gaseous fuel and, most preferably, a gaseous fuel is methane or natural gas. The natural gas is enhanced with hydrogen. As shown in FIG. 1, hydrogen stream 20 is combined with natural gas stream 22 to produce an enhanced combustion mixture which may be hythane. The hythane is stored in storage vessel 24 until needed and is fed to the reactor via stream 24a.

The enhanced natural gas may contain from about 10% to about 20% hydrogen and, more preferably about 15% hydrogen based upon volume.

The hythane is fed to cogeneration reactor 10 together with combustion air which may contain from about 0% to about 30% oxygen and, more preferably about 15% oxygen on a volume basis. As shown in FIG. 1, air stream 26 may be combined with oxygen stream 28 in vessel 30. The combined stream of oxygen and air, namely stream 32 is then fed to cogeneration reactor 10. Alternately, the air and oxygen may be separately fed to cogeneration reactor 10.

As shown in FIG. 1, the hythane and combined air/oxygen stream 32 may be fed either into a combustion turbine or into a steam turbine generator designated by reference numeral 34. The combustion of the hythane with air/oxygen stream 32 results in the production of process steam 40, stack gases 42 and electricity 44. In particular, the power take-off from the combustion turbine or the steam turbine generator is transmitted to alternating current generator 45a to produce electricity 44. Electricity 44 may then be fed to a direct current rectifier 45b to produce a direct electrical current 45c which is used to power electrolysis cell 12.

As discussed above, cogeneration reactor 10 may be either a single cycle or a combined cycle reactor. A typical combined cycle cogeneration process utilizing a combustion turbine is shown in FIG. 3 and a typical single cycle cogeneration process using a steam turbine is shown in FIG. 4.

Figure 3:
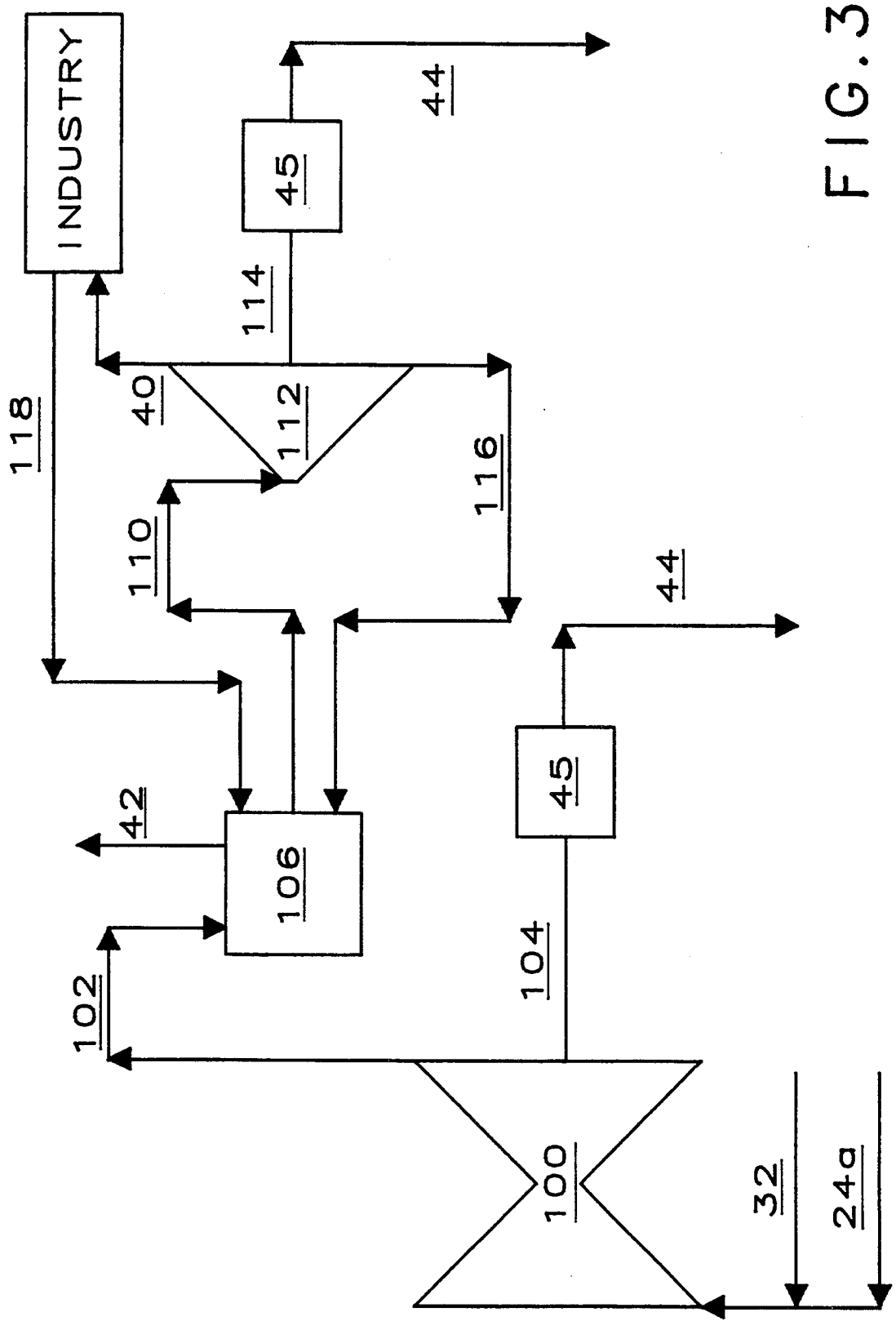
FIG. 3 is a schematic of a process flow sheet for a combined cycle cogeneration process; and, FIG. 4 is a schematic of a process flow sheet for a single cycle cogeneration process.

Referring to FIG. 3, a combined cycle cogeneration process utilizes combustion turbine 100. Fuel 24a and air/oxygen stream 32 are fed into combustion turbine 100. The combustion of the fuel in combustion turbine 100 produces combustion gas 102 and power. The power is transmitted to generator 45 via power take-off 104. The rotation of the turbine as transmitted through power take-off 104 causes generator 45 to produce electricity 44. Combustion gas 102 from combustion turbine 100 is fed to heat recovery boiler 106. Heat recovery boiler 106 effectively acts as a heat exchanger transferring the heat from the combustion gas to water in the recovery boiler 106. The combustion gases, which have been cooled, are then vented from boiler 106 as stack gases 42. The transfer of heat from combustion gas 102 to the water in heat recovery boiler 106 produces steam 110. Steam 110 is fed to steam turbine 112. As steam 110 passes through steam turbine 112, the steam causes the turbine to rotate. This rotation is transmitted to generator 45 via power take-off 114 which causes generator 45 to produce electricity 44. As steam passes through steam turbine 112, part of the steam condenses and this condensate is returned to heat recovery boiler 106 via return stream 116. The remainder of the steam, which is at a lower temperature and pressure than steam 110, may be used as process steam in the industry or in further subsequent steps as discussed hereinbelow. The process steam is fed to the remainder of the plant via feed stream 40. The steam which is used for heating purposes in the plant is recycled to boiler 106 via return stream 118. Make up water is added to boiler 106 as required (not shown).

Figure 4:
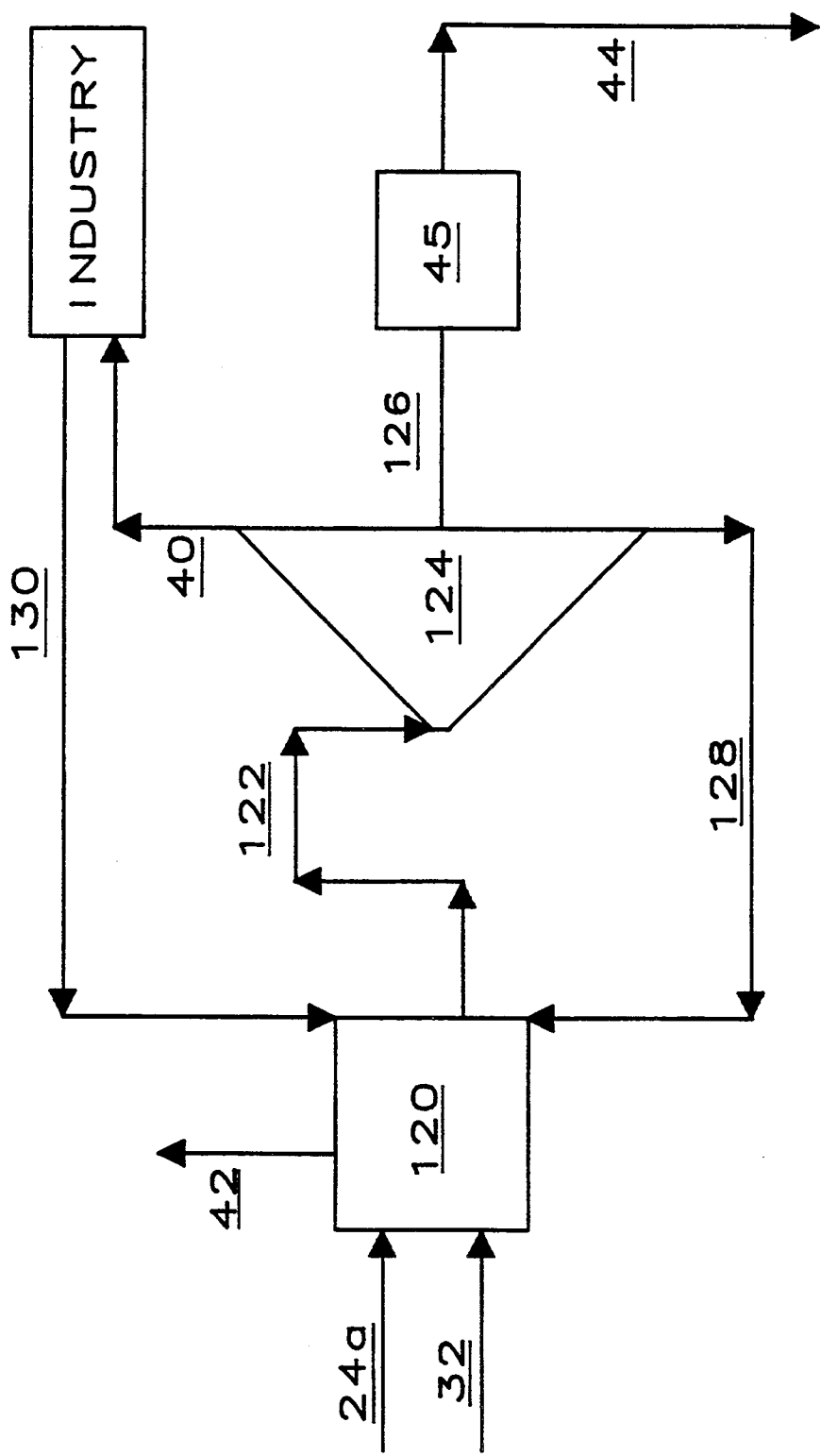

Referring to FIG. 4, a single cycle cogeneration process utilizes steam boiler 120. Fuel 24a and air/oxygen stream 32 are fed into steam boiler 120. The combustion of the fuel in steam boiler 120 produces stack gases 42 and steam 122. Steam 122 is fed into steam turbine 124. As steam 122 passes through steam turbine 124, the steam causes the turbine to rotate. This rotation is transmitted to generator 45 via power take-off 126. The rotation of power take-off 126 causes generator 45 to produce electricity 44. As steam 122 passes through steam turbine 124, part of the steam condenses and this condensate is returned to boiler 120 via return stream 128. The remainder of the steam, which is at a lower temperature and pressure than steam 122, may be used as process steam in the industry or in further subsequent steps as discussed hereinbelow. The process steam is fed to the remainder of the plant via feed stream 40. The steam which is used for heating purposes in the plant is recycled to steam boiler 120 via return stream 130. Make up water is added to steam boiler 120 as required (not shown).

The cogeneration reactor may be operated by an industry which requires process steam and electricity to run a plant. Accordingly, process steam 40 may be used in the plant for heating or other purposes as needed. Similarly, electricity 44 may be used in a plant or transmitted to a power grid 46 for sale to other consumers of electricity as needed. Alternately, part of the electricity may be used by electrolysis cell 12 to electrolyze water to produce hydrogen and oxygen. Electrolysis is very energy intensive and accordingly requires a large volume of electricity. Typically, it is not economically feasible to produce hydrogen and oxygen via electrolysis for use in a combustion. According to the instant invention, the electricity which is used in electrolysis cell 12 is surplus electricity which may be available in off-peak hours. For example, the cogeneration reactor may be operated on a continual basis to maintain process steam for use in a plant. However, the demand for electricity may drop off at night or on weekends. In these off-peak hours, the electricity may not be required on power grid 46. At such times, the electricity may be used to run electrolysis cell 12. Accordingly, one advantage of the instant invention is that it provides a means for greatly increasing the utilization of electrical generating apparatus which, by producing oxygen and hydrogen, results in the production of chemical energy sources for use immediately or at a later date. A second advantage of the instant invention is that the electrical output may be immediately transferred to conventional uses allowing the electrical output to serve as stand by power known in the industry as "synchronous spinning reserves".

As discussed above, electrolysis cell 12 is used to electrolyze water to produce hydrogen and oxygen. Make up water 12a is added to electrolysis cell 12 as required. The hydrogen and oxygen are separated by conventional means and are transferred to vessels 48 and 50 respectively. The hydrogen and oxygen may then be compressed by compressors 52 and 54 respectively. The compressed oxygen may then be stored in storage vessel 56. Similarly, the hydrogen may be stored in hydrogen storage vessel 58. Currently, expensive equipment is required to store hydrogen produced via electrolysis for long periods of time. Accordingly, the compressed hydrogen may be stored temporarily separately in vessel 58 and then sent directly via process stream 20 to combine with natural gas 22 to form hythane which may then be stored in storage vessel 24 for later use. Oxygen is fed via process stream 28 to mix with air for addition to cogeneration reactor 10.

It will be apparent from the foregoing that the electrolysis produces hydrogen and oxygen, at least a portion of each of which are added as feed materials to the reactor. The oxygen may be stored separately in vessel 56. Similarly, the hydrogen may be stored separately in vessel 58 or alternately combined with natural gas to form hythane and stored separately.

A portion of the hydrogen may not required as a fuel source. Accordingly, some of the hydrogen may be fed via second hydrogen stream 60 for use elsewhere in the plant or for methanol production as discussed hereinbelow. Similarly, all or a portion of the oxygen may not be required as combustion air. Accordingly, a second stream of oxygen 62 may be provided. This portion of the oxygen may be used elsewhere in the plant or sold for use by others.

The use of the cogeneration reactor and the electrolysis cells produces a synergistic result. Electrolysis cell 12 is preferably powered with electricity which is available in off-peak hours when the demand for electricity is otherwise low. The electricity in off-peak hours is of low economic benefit. By using this electricity to power electrolysis cell 12, hydrogen and oxygen are produced which can be used immediately or at a later date. Normally, hydrogen and oxygen are stored for later use. The addition of the hydrogen and oxygen provides additional fuel for the reactor, thus effectively changing the electricity to stored chemical energy, and results in the production of cleaner stack gases. By using a hydrogen enhanced gaseous fuel, preferably natural gas, a relatively clean stream of carbon dioxide is provided in stack gases 42. The stack gases accordingly contain a sufficiently pure stream of carbon dioxide which may be recovered and used as a feed stream for further processing.

The further processing alternatives which may be utilized for the carbon dioxide recovered from stack gases 42 and process steam 40 are set out in particular in FIG. 2. Referring to FIG. 2, carbon dioxide which is recovered from stack gases 42, steam from process steam 40 and hydrogen 60 may be added to methanol synthesizer 64 to produce methanol (process stream 66). Methanol stream 66 may be stored or sold as a commodity into the market-place. Alternately, some or all of methanol stream 66 may be reformed in methanol reformer 68 with additional process steam 40 to produce methyl tertiary butyl ether.

Primary and secondary fermenters 70 and 72 may be provided. Agricultural products, such as corn, wheat and barley may be added to primary fermenter 70. Process steam 40 may be added to primary fermenter 70 to produce ethanol (process stream 74) and carbon dioxide (process stream 76).

Similarly, wood waste, straw or cellulose separated from municipal solid waste may be added to secondary fermenter 72. Process stream 40 is also added to secondary fermenter 72 to produce ethanol (process stream 78) and carbon dioxide (process stream 80).

Carbon dioxide from process streams 76 and 80 may be combined with the carbon dioxide recovered from stack gases 42 and utilized in methanol synthesizer 64. Ethanol streams 74 and 78 may be combined and stored for use elsewhere in the plant or for sale. Alternately, ethanol with a portion of process steam 40 may be added to ethanol reformer 82 for the production of ethyl tertiary butyl ether.

In summary, off-peak electricity from the cogeneration process is used to produce hydrogen and oxygen which may be used to reduce the amount of impurities in stack gas 42 resulting in the production of a relatively clean stream of carbon dioxide. Carbon dioxide may be recovered from this stream and used to prepare methanol. The carbon dioxide may be supplemented with carbon dioxide from primary and secondary alcohol fermentation processes. The methanol may be reformed in whole or in part, utilizing cogenerated process steam to produce MTBE. Similarly, process steam may be utilized in primary and secondary alcohol fermenters to produce ethanol which, may be, in whole or in part, reformed to ETBE.

The process provides an integrated approach to produce a relatively pure stream of carbon dioxide by using off-peak electricity to power electrolysis cells. Further, process steam may be utilized to operate primary and secondary alcohol fermenters, the methanol synthesizer and/or the ethanol and ethanol reformers. The combination of these elements, and in particular the electrolysis and the cogeneration reactor produce a synergism which is not otherwise obtainable.

I claim:

1. A synergistic cogeneration process for the production of carbon dioxide, oxygen and hydrogen comprising the steps of:
   (a) preparing a feed stream comprising an organic combustible fuel and hydrogen;
   (b) introducing said feed stream and air into a cogeneration reactor for combusting said feed stream and producing steam, electricity and stack gases containing carbon dioxide, said reactor having a generator and means for combusting said feed stream drivingly connected to said generator via shaft means;
   (c) using electricity to electrolyze water to produce hydrogen and oxygen;
   (d) recovering said hydrogen from step (c) and recycling at least a portion of said hydrogen to step (a) for preparation of said feed stream; and,
   (e) recovering said carbon dioxide from said stack gases.

2. The process as claimed in claim 1 wherein said organic combustible fuel is a gaseous fuel.

3. The process as claimed in claim 2 wherein said gaseous fuel comprises methane.

4. The process as claimed in claim 3 wherein said gaseous fuel is natural gas.

5. The process as claimed in claim 3 wherein said oxygen is recovered from electrolysis step (c) and at least a portion of said oxygen is recycled to step (b) for introduction into said reactor.

6. The process as claimed in claim 5 wherein at least a portion of said electricity used to power electrolysis step (c) is produced in off-peak time.

7. The process as claimed in claim 6 wherein said feed stream comprises from about 10% to about 20% hydrogen on a volume basis.

8. The process as claimed in claim 7 wherein said feed stream contains about 15% hydrogen on a volume basis.

9. The process as claimed in claim 7 wherein said feed stream is combusted in air and from about 0% to about 30% oxygen on a volume basis.

10. The process as claimed in claim 9 wherein said feed stream is combusted with air and about 15% oxygen on a volume basis.

11. The process as claimed in claim 9 further comprising the step of adding at least a portion of said carbon dioxide recovered in the step (e) to a methanol synthesizer to produce methanol.

12. The process as claimed in claim 11 further compressing the step of reforming at least a portion of said methanol to produce methyl tertiary butyl ether.

13. The process as claimed in claim 11 wherein said cogeneration reactor is a single cycle cogenerator.

14. The process as claimed in claim 11 wherein said cogeneration reactor is a combined cycle cogenerator.

15. The process as claimed in claim 9 wherein at least a portion of said steam is added to a fermenter together with an alcohol precursor to produce ethanol.

16. The process as claimed in claim 15 further comprising the step of reforming at least a portion of said ethanol to produce ethanyl tertiary butyl ether.

17. A synergistic cogeneration process for the production of methanol comprising the steps of:
(a) preparing a feed stream comprising an organic combustible fuel and hydrogen;
(b) introducing said feed stream and air into a cogeneration reactor for combusting said feed stream and producing steam, electricity and stack gases containing carbon dioxide, said reactor having a generator and means for combusting said feed stream drivingly connected to said generator via shaft means;
(c) electrolyzing water to produce hydrogen and oxygen;
(d) recovering said hydrogen from step (c) and recycling at least a portion of said hydrogen to step (a) for preparation of said feed stream;
(e) recovering said carbon dioxide from said stack gases; and,
(f) adding at least a portion of said carbon dioxide recovered in the step (e) to a methanol synthesizer to produce methanol.

18. The process as claimed in claim 17 wherein said oxygen is recovered from electrolysis step (c) and at least a portion of said oxygen is recycled to step (b) for introduction into said reactor.

19. The process as claimed in claim 18 wherein said organic combustible fuel is a gaseous fuel.

20. The process as claimed in claim 19 wherein a portion of the electricity produced in step (c) is used to power electrolysis step (c).

21. The process as claimed in claim 17 wherein at least a portion of said electricity used to power electrolysis step (c) is produced in off-peak time.

* * * * *